US006919070B1

(12) United States Patent
Rudin et al.

(10) Patent No.: US 6,919,070 B1
(45) Date of Patent: *Jul. 19, 2005

(54) STOMATIC COMPOSITION

(75) Inventors: Vsevolod Nikolaevich Rudin, Moscow (RU); Vladislav Petrovich Zuev, Moscow (RU); Vladimir Fedorovich Komarov, Moscow (RU); Igor Vitallevich Melikhov, Moscow (RU); Vladimir Vasillevich Minaev, Moscow (RU); Andrei Yurlevich Orlov, Moscow (RU); Anatoly Aleksandrovich Mishin, Moscow (RU); Viktor Evgenievich Bozhevolnov, Moscow (RU)

(73) Assignee: Zakrytoe Aktsionernoe Obschestvo "OSTIM", Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 09/529,742

(22) PCT Filed: Oct. 17, 1997

(86) PCT No.: PCT/IB97/01634

§ 371 (c)(1),
(2), (4) Date: Jun. 24, 2000

(87) PCT Pub. No.: WO99/20237

PCT Pub. Date: Apr. 29, 1999

(51) Int. Cl.[7] ............................ A61K 7/16; A61K 7/18; A61K 7/20; A61F 13/00
(52) U.S. Cl. ............................ 424/49; 424/52; 424/57; 424/58; 424/400; 424/401; 424/435; 424/489; 424/601; 424/602; 514/835; 514/900; 514/901; 514/902
(58) Field of Search ............................ 424/49–58, 401; 433/228.1; 423/308; 106/35

(56) References Cited

U.S. PATENT DOCUMENTS 4,327,079 A  *  4/1982  Aoki .......................... 424/57
4,451,235 A  *  5/1984  Okuda et al. ................. 106/35
4,503,157 A  *  3/1985  Hatahira ....................... 501/1
4,587,120 A  *  5/1986  Ozawa et al. .................. 424/57
4,634,589 A  *  1/1987  Scheller ......................... 424/49
4,710,372 A  * 12/1987  Scheller ......................... 424/57
4,743,274 A  *  5/1988  Ozawa et al. .................. 51/309
4,933,171 A  *  6/1990  Bristow et al. ................. 424/57
4,933,173 A  *  6/1990  Bristow et al. ................. 424/57
4,988,499 A  *  1/1991  Bristow et al. ................. 424/52
5,089,254 A  *  2/1992  Coulson ....................... 424/57
5,112,599 A  *  5/1992  Coulson ....................... 424/57
5,134,009 A  *  7/1992  Ichitsuka et al. ............. 428/113
5,135,396 A  *  8/1992  Kuboki ........................ 424/49
5,227,147 A  *  7/1993  Yoshimura et al. .......... 423/308
5,240,659 A  *  8/1993  Ichitsuka et al. .............. 264/63
5,652,056 A  *  7/1997  Pepin ......................... 428/364
5,702,677 A  * 12/1997  Shimp et al. ............... 423/308
5,783,217 A  *  7/1998  Lee et al. .................... 424/602
5,833,959 A  * 11/1998  Atsumi et al. ................ 424/57
5,935,275 A  *  8/1999  Burgard et al. ........... 23/295 R
6,013,591 A  *  1/2000  Ying et al. ..................... 501/1
6,027,716 A  *  2/2000  Levin et al. .................. 424/58
6,254,855 B1 *  7/2001  Rudin et al. .................. 424/48

FOREIGN PATENT DOCUMENTS

| EP | 0499299 A2 | * | 8/1992 | |
| EP | 0 664133 | | 7/1995 | .......... A61L/27/00 |
| EP | 0 786 245 A1 | | 7/1997 | .......... A61K/7/16 |
| WO | 98/18719 | * | 5/1998 | |
| WO | WO 98/18719 | | 5/1998 | .......... C01B/25/32 |
| WO | 99/20237 | * | 4/1999 | |
| WO | 00/37033 | * | 6/2000 | |
| WO | 01/54746 A2 | * | 8/2001 | |

* cited by examiner

Primary Examiner—Frederick Krass

(57) ABSTRACT

A stomatic composition has particles of hydroxyapatite with an average particle size in length (l), width (d) and thickness (h) of: l from 0.2 μm to about 0.01 μm, d from about 0.1 μm to about 0.001 μm and h from about 0.1 μm to about 0.001 μm.

9 Claims, No Drawings

STOMATIC COMPOSITION

CROSS-REFERENCES TO RELATED APPLICATIONS

This application is a 371 of PCT/IB97/01634, filed Oct. 17, 1997.

STATEMENT REGARDING FEDERALLY SPONSORED RESEARCH OR DEVELOPMENT

Not applicable.

BACKGROUND OF THE INVENTION

This invention relates to the field of medicine, and in particular to the field of stomatology and may be used for preventive treatment of caries, parodenitis and paradentosis.

TECHNICAL FIELD

Industrial Application

The stomatic composition can be used to cure microdefects of the basic substance of the dental enamel, e.g. to prevent the spread of caries, and is also useful for preventive measures avoiding the spread of inflammable-destructive diseases of paradentium tissues, such as pardenitis and paradentosis.

The stomatic composition can be used in the form of tooth pastes, tooth creams and gels. Moreover, the composition can be included as a component in chewing gum, pastilles, tooth elixir and formulations to rinse mouth.

The stomatic composition according to the invention is capable to stimulate reparative osteogenesis processes and possessing a high bioactivity and specific pharmacological activity. Moreover, this composition is useful for combatting dental caries and to prevent the spread of such inflammable-destructive diseases of paradentium tissues as paradenitis and paradentosis, on the basis of hydroxyapatite also optionally comprising abrasive materials, humectants, thickeners, surfactants, flavouring agents, and a number of optional ingredients.

For these above-captioned purposes, stomatic compositions comprising hydroxyapatite (HA) have found an extensive application in the stomatologic practice.

There are certain compositions having a favourable effect including synthetic HA containing 92 to 97% $Ca_{10}(PO_4)_6(OH)_2$, 3 to 6% $H_2O$ and 0,3% $CaCO_3$ with an average particle size of 1 to 15 im.

Such a stomatic composition, for instance, according to Patent EP 0344832 cl. A61K 7/16, comprises save the stated HA, water-soluble casein material or sodium trimetaphosphate, as an anti-caries agent and also other well known ingredients which depend upon the forms of the product manufactured, such as vanous humectants, binding thickeners, surfactants, flavouring agents.

The known stomatic composition (EP 03442746 cl. A61K 7/18, publ.23.11.89) supplementary includes a fluorine-containing compound in the form of NaP or sodium monophluorphosphate as an anti-caries agent.

The amount of HA present in the stomatic composition is in the range of 1 to 50%, usually 2 to 20% by weight of the stomatic composition. The stomatic composition comprises some other ingredients: humectants, thickeners, surfactants and flavouring agents commonly known to those skilled in the art in all formulations of such products.

However, the stomatic compositions stated possess a relatively poor anti-caries effect and is not useful in the preventive medicine and in the treatment of inflammatory-destructive diseases of paradentium tissues.

SUMMARY OF THE INVENTION

It is an object of the present invention to create a stomatic composition comprising compounds capable to cure microdefects of the basic substance of the dental enamel to combat caries developing (e.g. to provide an anti-caries activity) and to prevent the spread of such inflammable-destructive diseases of paradentium tissues as paradenitis and paradentosis, and also compounds capable to stimulate reparative osteogenesis processes and possessing high bioactivity and specific pharmacological activity.

It is a further object of the invention to create a stomatic composition being identic to the basic substance of the dental enamel in its substance contents and crystalline parameters, as the acid formed in the materials covering dental surfaces causes destruction of mineral hydroxyapatyte out of which enamel is composed and has a result due to which calcium ion loss occurs.

DETAILED DESCRIPTION OF THE INVENTION

The task surprisingly has been solved in a composition characterised in that it comprises particles of hydroxyapatite with an average particle size in length (l), width (d) and thickness (h) of: (l) from about 0.2 $\mu$m to about 0.01 $\mu$m, (d) from about 0.1 $\mu$m to about 0.001 $\mu$m, and (h) from about 0.1 $\mu$m to about 0.0001 $\mu$m with the particles of hydroxyapatite having a specific surface of hydroxyapatite from 100 m$^2$/g to 150 m$^2$/g.

A preferred composition having a more pronounced effect in view of the improvements obtained according to the invention comprises particles of hydroxyapatite with an average particle size in length (l), width(d) and thickness(h) of about 1=0,06 im +/−50%, d=0,015im +/−50% and h=0,005 im +/−50%.

A most preferred composition having a surprisingly superior effect in view of the improvements obtained according to the invention comprises particles of hydroxyapatite with an average particle size in length (l), width(d) and thickness (h) of 1 about 0,06 im, d about 0,015 im, h about 0,005 im.

Being introduced into the composition, HA possesses osteo-reparative properties and contains preferably about 100% $Ca_{10}(PO_4)_6(OH)_2$.

The specific surface of HA used in the composite advantageously is 100 to 150 m$^2$/g.

U.S. Pat. No. 6,254,855 column 2, line 30 to column 4, line 35 which is based on WO 98/18719 (of the same inventor) are hereby incorporated by reference into the present application. The pages of U.S. Pat. No. 6,254,855 describe a method for producing a suspension of hydroxyapatite as described in this application.

The amount of HA present in the oral composition of the present invention is in the range of 0,1% to 50%, preferably from 0,1% to 25%, and most preferably from about 0,2% to 20% by weight of the oral composition.

The composition reacts to a change in the biochemical environment, for instance a rapid dissolvement of ultra finely divided HA occurs when the pH is decreasing, that provides an active utilization of Ca and $PO_4$—ions in the osteogenesis process: the size and configuration of the inventive crystals are adapted to the maximum to the dental enamel structure, which is mostly composed of HA that suggests its use in the osteo-reparative process as a building material.

The ultra finely divided HA possesses a high adhesive-sorption activity to the dental enamel and to microdefects on its surface, that favour the preventive measures preventing the spread of caries disease and also possesses a high sorption activity in respect to proteins and aminoacids of paradentium tissues, that stimulates an active preventive treatment of the inflammable-destructive diseases such as paradenitis and paradentosis.

Moreover, the stomatic composition of the present invention will contain other conventional ingredients in addition to HA possessing osteo-reparative properties, whose introduction into the composition depends on the form of he product. For instance, in the case of an oral product in the form of dentifrice paste, cream or gel, the product will comprise a liquid phase containing humectants and binding thickeners which act to maintain the particulate solid abrasive and HA crystals in the form of stable suspension in the liquid phase.

Surfactants and flavouring agents are also usual ingredients for various inventive embodiments of oral compositions.

The humectants usually used are glycerol or sorbitol. However, other humectants may be used according to the invention including polyethyleneglycol, propyleneglycol, lactitol and hydrogenated corn syrup. The amount of hunctant will generally range from about 0% to 85% by weight of product. The remainder of the liquid phase will consist substantially of water. The liquid phase can be water or a non-aqueous composition.

As binding agents and thickeners, various substances can be used such as sodium carboxymethylcellulose, sodium hydroxyethytcellulose and xanthan gum. Natural gum bindings can be included such as gum tragacanth, gum karaya of Irish moss, etc. Any mixture of binding agents and thickeners can be also used. The amount of bindings and thickeners usually included into the oral composition is in the range of 0% to 10% by weight of the oral composition.

Moreover, any materials as widely disclosed in the literature generally also might be used for the invention as surfactants, i.e. surfactants like sodium lauryl sulphate, dodecylbenzene sulphonate and sodium lauryl sarcosinate. Other anionic surfactants also can be used as well as cationic and amphoteric and non-ionic surfactants. Surfactants are generally present in the composition in the amount of 0% to 5% by weight of the oral composition.

Flavours that are generally used in the oral compositions are those based on oils of spearmint and peppermint and might be used for the invention. Examples of other flavouring materials used are menthol, clove, wintergreen, eucalyptus and aniseed. A preferable amount of flavours is from 0% to 5% by weight in respect to the oral composition.

As abrasive materials, silica dioxide of various modifications, aluminium oxide, calcium carbonate, dicalcium phosphate anhydrite, dicalcium phosphate dihydrate, sodium metaphosphate insoluble in water, and thereof mixtures may be used. The amount of abrasive materials ranges from 0.0% to 25%. The oral composition may include a wide variety of optional ingredients. These include antimicrobial and anti-plaque agents for example chlorhexidine or 2,4,4-trichloro-2hydroxy-diphenyl ether, or zink compounds (see EPA-161898) anti-tartar ingredients such as condensed phosphates, e.g. alkali et al pyrophosphates, hexametaphosphatesor polyphosphates (see U.S. Pat. No. 4,515,772 and U.S. Pat. No. 4,627,977) or zinc citrates (see U.S. Pat. No. 4,100,269), sweetening agents such as saccharin. Preservatives such as formalin, sodium benzoate. colouring agents (for instance titanium dioxide) or pH-controlling agents, such as acid base or buffer agents the oral composition may also include agents enhancing the gingivitis system of the mouth cavity and representing extracts of various natural plants such as urtica, millefolium, chamomilla hypericum, salvia, etc. in the aqueous or aqueous-alcoholic forms.

The stomatic composition depending on its form (dentifrice paste, cream or gel) is maintained in contact with the tissue of the oral cavity from 15 sec to 12 hours.

The following examples of dentifrice pastes and gel comprising synthetic ultra finely divided HA possessing osteo-reparative properties as described above illustrate the invention. Percentages and parts of the components are by weight.

Below-standing preferred embodiments of the invention are shown in its composition.

EXAMPLES N1 AND 2.

Toothpaste prepared from the following ingredients.

|  | Ingredients, % | |
| --- | --- | --- |
| Example | 1 | 2 |
| Ultra finely divided Hydroxyapatite | 0.2 | 2.0 |
| Silica aerogel | 22.0 | 15.0 |
| Sodium carboxymethylcellulose | 1.0 | 1.0 |
| Glycerol distilled | 20.0 | 20.0 |
| Sorbitol | 20.0 | 17.0 |
| Titanium dioxide | 0.6 | 0.5 |
| Sodium benzoate | 0.4 | 0.6 |
| Aqueous-alcohol extract of chamomilla | 1.0 | 0.8 |
| Aqueous-alcohol extract of hypericum | 1.0 | 0.8 |
| Sodium saccharin | 0.1 | 0.06 |
| Flavour | 1.0 | 1.3 |
| Sodium lauryl sulphate | 1.5 | 1.5 |
| Water | to 100.0 | to 100.0 |

EXAMPLES N 3 TO 7

Toothpaste prepared from the following ingredients.

|  | Ingredients, % | | | | |
| --- | --- | --- | --- | --- | --- |
| Example | 3 | 4 | 5 | 6 | 7 |
| Ultra finely divided hydroxyapatite | 2.5 | 2.5 | 2.5 | 2.5 | 2.5 |
| Silica aerogel | 17.0 | 17.0 | 17.0 | 17.0 | 17.0 |
| Sodium hydroxyethylcellulose | 1.6 | — | — | 1.6 | — |
| Sodium carboxymethylcellulose | — | 1.1 | 1.1 | — | 0.9 |
| Sorbitol | 20.0 | 20.0 | 16.0 | 20.0 | 20.0 |
| Glycerol distilled | 20.0 | 20.0 | 20.0 | 20.0 | 20.0 |
| Polyethyleneglycol | — | — | 5.0 | — | — |
| Sodium lauryl sulphate | 1.5 | 1.5 | 1.5 | 1.5 | 1.5 |
| Tetrasodium pyrophosphate | — | 1.5 | — | — | — |
| Tetrapotassium pyrophosphate | — | — | — | 2.5 | — |
| Sodium trimetaphosphate | — | — | 2.0 | — | — |
| Zinc citrate trihydrate | — | — | — | — | 0.5 |
| Titanium dioxide | 0.6 | 0.6 | 0.6 | 0.6 | 0.6 |
| Sodium benzoate | 0.5 | 0.5 | 0.6 | — | — |
| Formalin | — | — | — | 0.05 | 0.05 |
| Aqueous-alcohol extract of salvia | 0.5 | 0.5 | — | — | — |
| Aqueous-alcohol extract of millefolium | 0.9 | 0.9 | 0.5 | 0.5 | — |
| Aqueous-alcohol extract of chamomilla | — | — | 1.0 | 0.7 | — |
| Triclosan | — | — | 0.2 | — | 0.2 |
| Sodium saccharin | 0.06 | 0.06 | 0.06 | 0.06 | 0.06 |
| Flavour | 1.0 | 1.0 | 1.0 | 1.0 | 1.0 |
| Water (in all examples) to 100.0 | | | | | |

EXAMPLES N8 AND 9

Gel preventing paradenitis.

|  | Ingredients, % | |
| --- | --- | --- |
| Example | 8 | 9 |
| Ultra finely divided hydroxyapatite | 5.0 | 4.0 |
| Sodium hydroxyethylcellulose | 2.0 | 2.5 |
| Silica aero | 5.0 | — |
| Glycerol distilled | 10.0 | — |
| Sorbitol | 25.0 | 45.0 |
| Sodium benzoate | 0.5 | — |
| Triclosan | — | 0.3 |
| Flavour | 0.2 | 0.15 |
| Sodium lauryl sulphate | 0.2 | 0.15 |
| Sodium saccharin | 0.07 | 0.07 |
| Water | to100.00 | to100.00 |

What is claimed is:

1. A stomatic composition characterised in that it comprises particles of hydroxyapatite with an average particle size in length (l), width (d) and thickness (h) of: (1) from about 0.2 µm to about 0.01 µm, (d) from about 0.1 µm to about 0.001 µm, and (h) from about 0.1 µm to about 0.0001 µm with the particles of hydroxyapatite having a specific surface of hydroxyapatite from 100 m²/g to 150 m²/g.

2. The stomatic composition according to claim 1 characterised in that it comprises particles of hydroxyapatite with an average particle size in length (l), width (d) and thickness (h) of about (1)=0.06 µm +/−50%, (d)=0.015 µm +/−50% and (h)=0.005 µm +/−50%.

3. The stomatic composition according to claim 1 characterised in that it comprises particles of hydroxyapatite with an average particle size in length (l), width (d) and thickness (h) of about (l)=0.06 µm, (d)=0.015 µm, (h)=0.005 µm.

4. The composition according to claim 1 characterised in that the hydroxyapatite particles are present in the composition in an amount of 0.1% to 50% by weight, based on the weight of the stomatic composition.

5. The composition according to claim 1 characterised in that the hydroxyapatite is a synthetic hydroxyapatite which contains 99.9% of $Ca_{10}(PO_4)_6(OH)_2$ by weight.

6. The composition according to claim 1 further comprising at least one substance selected from the group consisting of humectants in a range from about 0% to 85% by weight, binders and thickeners in a range of 0% to 10% by weight, abrasive materials in a range from 0.0% to 25%, surfactants in a range from 0% to 5% by weight, flavours in a range from 0% to 5% by weight, based on the weight of the composition.

7. The composition according to claim 1 further comprising gingivitis treating agents comprising extracts of natural plants selected from the group consisting of urtica, millefolium, chamomilla hypericum, salvia, and in an aqueous or an aqueous-alcoholic form.

8. The composition according to claim 1 further comprising effective amounts of anti-microbial and anti-plaque agents.

9. A stomatic composition comprising particles of hydroxyapatite with an average particle size in length (l), width (d) and thickness (h) of: (l) from about 0.2 µm to about 0.01 µm, (d) from about 0.1 µm to about 0.001 µm, and (h) from about 0.1 µm to about 0.0001 µm, and effective amounts of gingivitis treating agents comprising extracts of natural plants selected from the group consisting of urtica, millefolium, chamomilla hypericum, and salvia, in an aqueous or an aqueous-alcoholic form.

* * * * *